United States Patent
Lewis

(10) Patent No.: US 10,527,847 B1
(45) Date of Patent: Jan. 7, 2020

(54) DIGITAL EYEWEAR

(71) Applicant: Percept Technologies Inc., Los Altos, CA (US)

(72) Inventor: Scott W. Lewis, Las Vegas, NV (US)

(73) Assignee: Percept Technologies Inc, Las Vegas, NV (US)

( * ) Notice: Subject to any disclaimer, the term of this patent is extended or adjusted under 35 U.S.C. 154(b) by 0 days.

(21) Appl. No.: 16/236,349

(22) Filed: Dec. 29, 2018

Related U.S. Application Data

(60) Continuation of application No. 16/166,171, filed on Oct. 22, 2018, which is a continuation of application No. 15/004,814, filed on Jan. 22, 2016, now Pat. No. 10,151,937, which is a continuation of application No. 14/660,497, filed on Mar. 17, 2015, now Pat. No. 9,244,293, which is a continuation of application No. 13/739,929, filed on Jan. 11, 2013, now Pat. No. 9,010,929, which is a continuation of application No. 13/078,589, filed on Apr. 1, 2011, now Pat. No. 8,353,594, which is a continuation of application No. 12/621,423, filed on Nov. 18, 2009, now Pat. No. 7,918,556, which is a continuation of application No. 12/029,068, filed on Feb. 11, 2008, now Pat. No. 7,758,185, which is a division of application No. 11/245,756, filed on Oct. 7, 2005, now abandoned.

(51) Int. Cl.
*G02C 11/00* (2006.01)
*G02B 27/00* (2006.01)
*G02B 27/01* (2006.01)
*H04R 5/033* (2006.01)

(52) U.S. Cl.
CPC ..... *G02B 27/0093* (2013.01); *G02B 27/0172* (2013.01); *G02C 11/10* (2013.01); *H04R 5/0335* (2013.01); *G02B 2027/0132* (2013.01); *G02B 2027/0138* (2013.01); *G02B 2027/0178* (2013.01)

(58) Field of Classification Search
CPC .......... G02C 11/00; G02C 11/06; G02C 11/10
See application file for complete search history.

(56) References Cited

U.S. PATENT DOCUMENTS

| | | | |
|---|---|---|---|
| 4,279,474 A | 7/1981 | Belgorod | |
| 4,300,818 A | 11/1981 | Schachar | |
| 5,212,677 A | 5/1993 | Shimote et al. | |
| 5,305,012 A | 4/1994 | Faris | |
| 5,552,841 A | 9/1996 | Gallorini et al. | |
| 5,583,795 A | 12/1996 | Smyth | |
| 5,617,035 A | 4/1997 | Swapp | |

(Continued)

*Primary Examiner* — Darryl J Collins

(57) ABSTRACT

Improved eyewear is disclosed. The eyewear comprises a frame member and a lens. The eyewear also includes circuitry within the frame member for enhancing the use of the eyewear. A system and method in accordance with the present invention is directed to a variety of ways to enhance the use of eyeglasses. They are: (1) media focals, that is, utilizing the eyewear for its intended purpose and enhancing that use by using imaging techniques to improve the vision of the user; (2) telecommunications enhancements that allow the eyeglasses to be integrated with telecommunication devices such as cell phones or the like; and (3) entertainment enhancements that allow the eyewear to be integrated with devices such as MP3 players, radios, or the like.

30 Claims, 6 Drawing Sheets

(56) References Cited

U.S. PATENT DOCUMENTS

| | | |
|---|---|---|
| 5,751,260 A | 5/1998 | Nappi et al. |
| 5,886,822 A | 3/1999 | Spitzer |
| 6,091,378 A | 7/2000 | Richardson et al. |
| 6,099,124 A | 8/2000 | Hidaji |
| 6,106,119 A | 8/2000 | Edwards |
| 6,222,508 B1 | 4/2001 | Alvelda et al. |
| 6,231,193 B1 | 5/2001 | Dillon |
| 6,307,526 B1 | 10/2001 | Mann |
| 6,603,443 B1 | 8/2003 | Hildebrand et al. |
| 6,608,615 B1 | 8/2003 | Martins |
| 6,647,269 B2 | 11/2003 | Hendry et al. |
| 6,836,669 B2 | 12/2004 | Miyake et al. |
| 7,370,016 B1 | 5/2008 | Hunter et al. |
| 7,436,568 B1 | 10/2008 | Kuykendall, Jr. |
| 7,486,926 B2 | 2/2009 | White et al. |
| 7,538,744 B1 | 5/2009 | Liu et al. |
| 7,539,175 B2 | 5/2009 | White et al. |
| 7,561,143 B1 | 7/2009 | Milekic |
| 7,651,220 B1 | 1/2010 | Pattikonda |
| 7,677,734 B2 | 3/2010 | Wallace |
| 7,693,384 B2 | 4/2010 | Lee et al. |
| 7,738,179 B2 | 6/2010 | Nishi |
| 7,758,185 B2 | 7/2010 | Lewis |
| 7,918,556 B2 | 4/2011 | Lewis |
| 8,238,926 B2 | 8/2012 | Lewis |
| 8,275,382 B2 | 9/2012 | Lewis |
| 8,353,594 B2 | 1/2013 | Lewis |
| 8,451,850 B2 | 5/2013 | Lewis |
| 8,566,894 B2 | 10/2013 | Lewis |
| 8,594,636 B2 | 11/2013 | Lewis |
| 8,696,113 B2 | 4/2014 | Lewis |
| 8,733,927 B1 | 5/2014 | Lewis |
| 8,733,928 B1 | 5/2014 | Lewis |
| 8,830,963 B2 | 9/2014 | Lewis |
| 8,885,882 B1 | 11/2014 | Yin et al. |
| 9,010,929 B2 | 4/2015 | Lewis |
| 9,061,025 B2 | 6/2015 | Burstein et al. |
| 9,230,292 B2 | 1/2016 | Amin et al. |
| 9,235,064 B2 | 1/2016 | Lewis |
| 9,239,473 B2 | 1/2016 | Lewis |
| 9,244,293 B2 | 1/2016 | Lewis |
| 9,264,319 B2 | 2/2016 | Lewis |
| 9,323,325 B2 | 4/2016 | Perez et al. |
| 9,363,541 B2 | 6/2016 | Lewis |
| D784,362 S | 4/2017 | Amin |
| 9,658,473 B2 | 5/2017 | Lewis |
| 9,740,552 B2 | 8/2017 | Lewis |
| 9,843,897 B1 | 12/2017 | Lin et al. |
| 10,021,430 B1 | 7/2018 | Lewis |
| 10,091,084 B2 | 10/2018 | Tao et al. |
| 10,093,252 B2 | 10/2018 | Zych |
| 10,151,937 B2 | 12/2018 | Lewis |
| 2001/0029583 A1 | 10/2001 | Palatov et al. |
| 2001/0055152 A1 | 12/2001 | Richards |
| 2002/0044152 A1 | 4/2002 | Abbott, III et al. |
| 2002/0046122 A1 | 4/2002 | Barber et al. |
| 2002/0056118 A1 | 5/2002 | Hunter et al. |
| 2002/0075210 A1 | 6/2002 | Nestorovic et al. |
| 2002/0101568 A1* | 8/2002 | Ebert ............... G02B 27/017 351/211 |
| 2002/0102993 A1 | 8/2002 | Hendrey et al. |
| 2002/0105482 A1 | 8/2002 | Lemelson et al. |
| 2002/0140899 A1 | 10/2002 | Blum et al. |
| 2002/0188219 A1 | 12/2002 | Suchard |
| 2003/0001981 A1 | 1/2003 | Milne |
| 2003/0071962 A1 | 4/2003 | Nishihara |
| 2003/0142041 A1 | 7/2003 | Barlow et al. |
| 2003/0161354 A1 | 8/2003 | Bader et al. |
| 2004/0108971 A1 | 6/2004 | Waldern et al. |
| 2004/0148551 A1 | 7/2004 | Kawahara |
| 2004/0156554 A1 | 8/2004 | McIntyre |
| 2005/0020910 A1 | 1/2005 | Quadling et al. |
| 2005/0049022 A1 | 3/2005 | Mullen |
| 2005/0057701 A1 | 3/2005 | Weiss |
| 2005/0175218 A1 | 8/2005 | Vertegaal et al. |
| 2005/0206583 A1 | 9/2005 | Lemelson et al. |
| 2005/0211764 A1 | 9/2005 | Barcelou |
| 2005/0246282 A1 | 11/2005 | Naslund et al. |
| 2005/0249196 A1 | 11/2005 | Ansari et al. |
| 2006/0023158 A1 | 2/2006 | Howell et al. |
| 2006/0023595 A1 | 2/2006 | Erickson et al. |
| 2006/0050232 A1 | 3/2006 | Dukes et al. |
| 2006/0075441 A1 | 4/2006 | Gauba et al. |
| 2006/0093998 A1 | 5/2006 | Vertegaal et al. |
| 2006/0132382 A1 | 6/2006 | Jannard |
| 2006/0140502 A1 | 6/2006 | Tseng et al. |
| 2006/0158639 A1 | 6/2006 | Campin et al. |
| 2006/0146275 A1 | 7/2006 | Mertz |
| 2006/0244908 A1 | 11/2006 | Cano |
| 2006/0282864 A1 | 12/2006 | Gupte |
| 2007/0002039 A1 | 1/2007 | Pendleton et al. |
| 2007/0143793 A1 | 6/2007 | Barratt et al. |
| 2007/0153498 A1 | 7/2007 | Wilt et al. |
| 2007/0161972 A1 | 7/2007 | Felberg et al. |
| 2007/0226575 A1 | 9/2007 | Zhang et al. |
| 2007/0282678 A1 | 12/2007 | Dendi et al. |
| 2008/0062378 A1 | 3/2008 | McCracken |
| 2008/0186449 A1 | 8/2008 | Sur et al. |
| 2008/0316605 A1 | 12/2008 | Hazell et al. |
| 2009/0103044 A1 | 4/2009 | Duston et al. |
| 2009/0207373 A1 | 8/2009 | Stinson |
| 2009/0209723 A1 | 8/2009 | Lesartre et al. |
| 2009/0216092 A1 | 8/2009 | Waldorf et al. |
| 2009/0268162 A1 | 10/2009 | Stetson et al. |
| 2010/0002191 A1 | 1/2010 | Drobe |
| 2010/0045928 A1 | 2/2010 | Levy |
| 2010/0067335 A1 | 3/2010 | Li et al. |
| 2010/0149073 A1 | 6/2010 | Chaum et al. |
| 2010/0305411 A1 | 12/2010 | Paul |
| 2011/0007275 A1 | 1/2011 | Yoo et al. |
| 2011/0213664 A1 | 9/2011 | Osterhout et al. |
| 2012/0019662 A1 | 1/2012 | Maltz |
| 2012/0021806 A1 | 1/2012 | Maltz |
| 2012/0088526 A1 | 4/2012 | Linder |
| 2012/0154277 A1 | 6/2012 | Bar-Zeev et al. |
| 2012/0229248 A1 | 9/2012 | Pashionikar et al. |
| 2012/0235902 A1 | 9/2012 | Eisenhardt et al. |
| 2012/0242678 A1 | 9/2012 | Border et al. |
| 2012/0293548 A1 | 11/2012 | Perez et al. |
| 2012/0293773 A1 | 11/2012 | Publicover et al. |
| 2012/0329764 A1 | 12/2012 | Burstein et al. |
| 2013/0117377 A1 | 5/2013 | Miller |
| 2013/0156265 A1 | 6/2013 | Hennessy |
| 2013/0293844 A1 | 11/2013 | Gross et al. |
| 2014/0002796 A1 | 1/2014 | Marcos Munoz |
| 2014/0303124 A1 | 10/2014 | Burstein et al. |
| 2014/0347265 A1 | 11/2014 | Aimone et al. |
| 2018/0177976 A1 | 6/2018 | Burstein |

\* cited by examiner

100

102'

400

DIGITAL EYEWEAR

CROSS-REFERENCE TO RELATED APPLICATION

According to 35 USC § 120, this application is a continuation application and claims the benefit of priority to U.S. patent application Ser. No. 16/166,171, filed Oct. 22, 2018, titled "DIGITAL EYEWEAR", now pending, which is a continuation application and claims the benefit of priority to U.S. patent application Ser. No. 15/004,814, filed Jan. 22, 2016, titled "DIGITAL EYEWEAR", now U.S. Pat. No. 10,151,937, issued Dec. 11, 2018, which is a continuation application and claims the benefit of priority to U.S. patent application Ser. No. 14/660,497, filed Mar. 17, 2015, titled "DIGITAL EYEWEAR", now U.S. Pat. No. 9,244,293, issued Jan. 26, 2016, which is a continuation application and claims the benefit of priority to U.S. patent application Ser. No. 13/739,929, filed Jan. 11, 2013, titled "DIGITAL EYEWEAR", now U.S. Pat. No. 9,010,929, issued Apr. 21, 2015, which is a continuation application and claims the benefit of priority to U.S. patent application Ser. No. 13/078,589, filed Apr. 1, 2011, titled "DIGITAL EYEWEAR", now U.S. Pat. No. 8,353,594, issued Jan. 15, 2013, which is a continuation of U.S. patent application Ser. No. 12/621,423, filed Nov. 18, 2009, titled "DIGITAL EYEWEAR", now U.S. Pat. No. 7,918,556, issued Apr. 5, 2011, which is a continuation of U.S. patent application Ser. No. 12/029,068, filed Feb. 11, 2008, titled "DIGITAL EYEWEAR", now U.S. Pat. No. 7,758,185, issued Jul. 20, 2010, which is a divisional application of U.S. patent application Ser. No. 11/245,756, filed Oct. 7, 2005, titled "DIGITAL EYEWEAR", now abandoned, issued Apr. 12, 2007, all of which are hereby incorporated by reference as if fully set forth herein.

FIELD OF THE INVENTION

The present invention relates generally to eyewear and more particularly to eyewear that includes additional functionality.

BACKGROUND OF THE INVENTION

Eyewear is utilized for a variety of purposes. Eyewear is used for improving one's vision for reading glasses and to protect one's vision. Oftentimes protective goggles are used to protect eyes within dangerous areas. It is desirable to add additional functionality to glasses. This functionality can include a variety of forms, which are electronic, mechanical, aesthetic, etc. Accordingly, it is always desired to provide additional functionality to eyewear. What is desired is a system and method which will increase the functionality of glasses beyond their normal use while still maintaining them for their primary uses. The present invention addresses such a need.

SUMMARY OF THE INVENTION

Improved eyewear is disclosed. The eyewear comprises a frame member and a lens. The eyewear also includes circuitry within the frame member for enhancing the use of the eyewear.

A system and method in accordance with the present invention is directed to a variety of ways to enhance the use of eyeglasses. They are:

(1) Media focals, that is, utilizing the eyewear for its intended purpose and enhancing that use by using imaging techniques to improve the vision of the user.

(2) Telecommunications enhancements that allow the eyeglasses to be integrated with telecommunication devices such as cell phones or the like.

(3) Entertainment enhancements that allow the eyewear to be integrated with devices such as MP3 players, radios, or the like.

DETAILED DESCRIPTION

The present invention relates generally to eyewear and more particularly to eyewear that includes additional functionality. The following description is presented to enable one of ordinary skill in the art to make and use the invention and is provided in the context of a patent application and its requirements. Various modifications to the preferred embodiments and the generic principles and features described herein will be readily apparent to those skilled in the art. Thus, the present invention is not intended to be limited to the embodiments shown, but is to be accorded the widest scope consistent with the principles and features described herein.

A system and method in accordance with the present invention is directed to a variety of ways to enhance the use of eyeglasses. There are three areas of eyeglass enhancement which are identified in the present application. They are:

(1) Media focals that is, utilizing the eyewear for its intended purpose and enhancing that use by using imaging techniques to improve the vision of the user.

(2) Telecommunications enhancements that allow the eyeglasses to be integrated with telecommunication devices such as cell phones or the like.

(3) Entertainment enhancements that allow the eyewear to be integrated with devices such as MP3 players, radios, or the like.

Finally, these features can be utilized together to provide a user with all of the above-enhanced features. To describe the features of the present invention in more detail refer now to the following description in conjunction with the accompanying figures.

1. Media Focals 100

Figure 1:
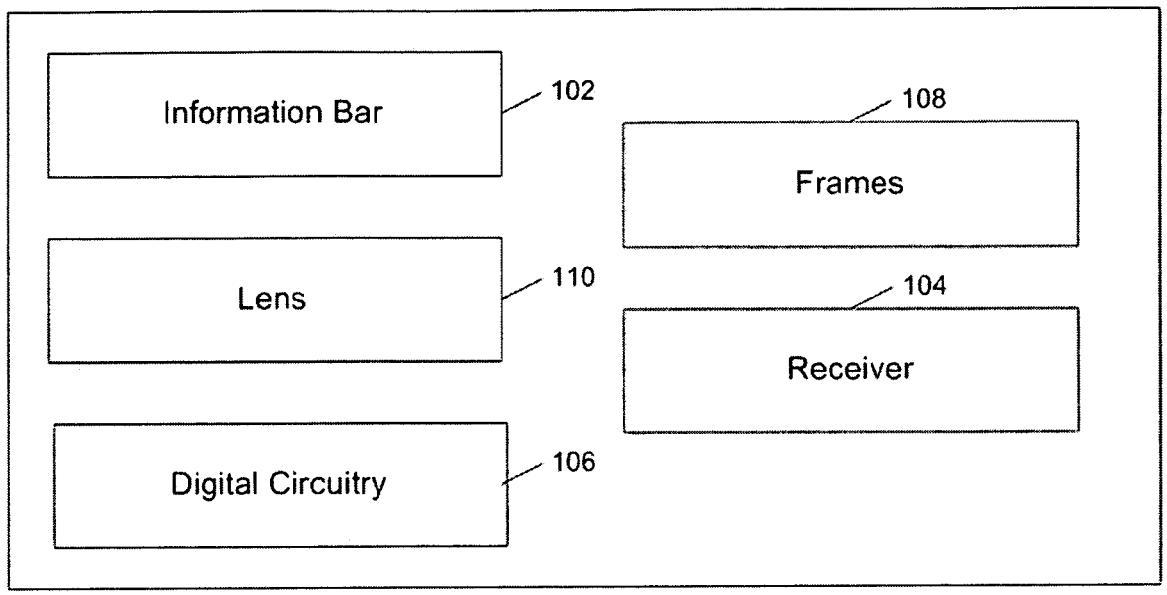
FIG. 1 is a diagram that illustrates Media focals.

FIG. 1 is a diagram that illustrates Media focals 100. Media focals 100 comprises an information bar 102, receiver 104, digital circuitry 106, frames 108 and lens 110. Media focals 100 allow for enhancing the eyewear for its primary purpose, for example, a digital camera could be placed within the eyewear to allow for seeing certain of these images. For example, the circuitry 106 for the media focals 100 could be placed within the frame 108 of the eyewear. The lens 110 could have a totally reflective surface, or a partially reflective surface using LCDs or the like. In effect the eyewear could look like see-through glasses, but through the use of the circuitry 106 within the eyewear it is actually a media focal. Additionally, the eyewear could incorporate a camera to project the user onto a second lens to achieve a see-through effect.

In a preferred embodiment, an information bar 102 is provided across a portion of the eyewear which is visible to the user. This information bar 102 is used to convey a variety of types of information.

Figure 2:
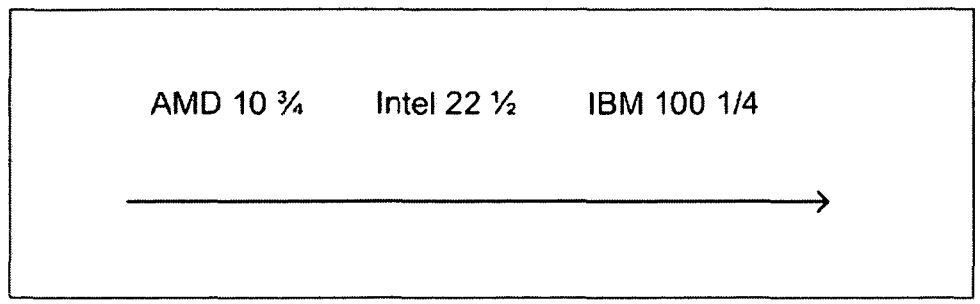
FIG. 2 illustrates an information bar on media focal eyewear.

FIG. 2 comprises an information bar 102' on media focal eyewear. The information bar 102' can be a stock ticker scrolling across the top portion of the eyewear, as is shown in FIG. 2. Although the information bar 102' is shown displaying a stock ticker, other kinds of information such as song titles, lyrics and the like could be displayed in the information bar. This information bar is referred to as E-focals. This information might be provided from a digital receiver through an FM station, through a cellular wireless device, or an MP3 player. Additional functionality of the E-focal will be described with more detail with respect to the cell phone enhancements as well as the music player enhancements.

One of the key features of the media focals 100 is the use of the media focals to enhance the primary function of the user, that is, being able to more accurately and clearly see the objects. In such an environment, for example, it is possible to have a zoom feature circuit to allow for the use of the eyewear as binoculars. This would allow for the user to see objects more closely based on certain activities of the user. For example, there may be eye or pressure sensors on the eyewear that will activate the binocular circuitry in the glasses which could receive visual data through a camera, CCD receiver of the like.

In the preferred embodiment, the circuitry 106 would be located somewhere in the frame of the glasses to provide this functionality and as circuits became smaller and devices became smaller it would be easier and easier to embed the circuitry that is well known for use for such functions directly within the device. The circuitry 106 in the device could be, for example, eye sensors which could be pressure sensors, capacitive sensors or some other type of sensor for allowing the eyes to direct the activities. Eye movement sensors, for example, could be used to activate and control the binocular glasses. Similarly, a digital camera could be put on the glasses that would allow the same kinds of technology to take pictures by the person directly.

In a similar vein, the glasses could be used as a normal corrective lens glass utilizing the digital imagery, so that, for example, a user has a certain prescription that they use with their normal prescription glasses to view an object clearly. As the user's eyes change, it would be possible that an optometrist could download the new prescription to the eyewear such that a digital transformation of the image information is provided which is compatible with the new prescription.

Also, in a preferred embodiment a method for sensing and controlling the digital media could be implemented in a variety of ways. For example, an activity of the eye itself would control the activity of the media focal. So, for example, if the idea was to zoom the image, the eye would blink twice. It would also be possible to detect facial and eye movements (squinting, for example), as well as changes in the pupil and iris.

In a further embodiment, it would be possible for the eyeglasses in accordance with the present invention to function within a client/server model or Bluetooth (wi fi) model. Utilization of the client/server model and Bluetooth wifi would make possible, for example, the display of live news or special reports (such as financial reports) from the Internet or similar sources on the eyeglasses. This would also allow for portions of circuitry to be located remotely such that less circuitry in the eyewear is required.

The eyewear could also include a logo, for example, law enforcement officers could have their glasses emblazoned with "Police", "Sheriff", "MP", etc.; young people could have their eyeglasses emblazoned with words and images that reflected their favorite performers, etc.; sports teams could offer the eyeglasses at discount with team monograms, etc. They could also be purchased by companies, emblazoned with the company logos, and given out as retirement gifts, etc.

2. Music Environment

Figure 3:
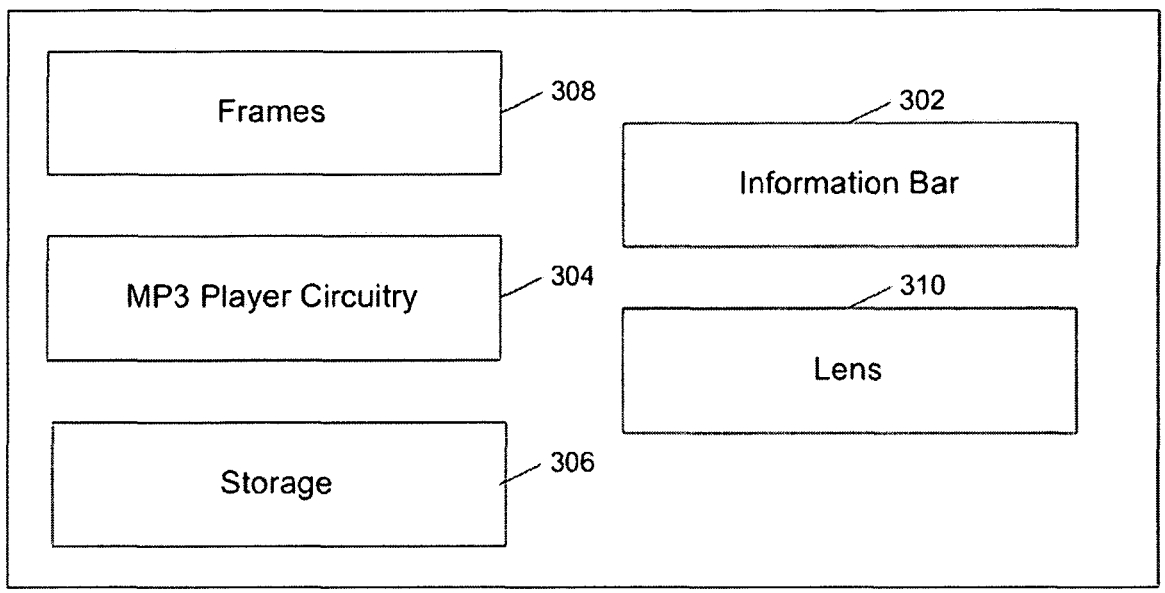
FIG. 3 is a block diagram of the features of eyewear that are utilized in a music environment such as an MP3 player.
Figure 3A:
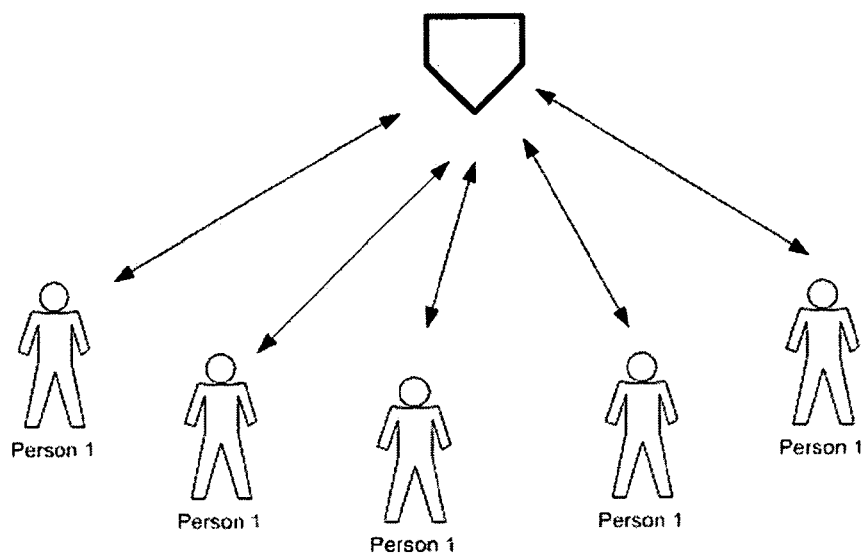
FIG. 3*a* illustrates a plurality of MP3 player eyewear users in a karaoke performance.

FIG. 3 is a block diagram of eyewear 300 that is utilized in a music environment such as an MP3 player. FIG. 3 comprises eyewear 300, an information bar 302, MP3 player circuitry 304, storage 306, frames 308, and one or a plurality of lenses 310. Another environment as has been above described is the music environment. What would be desirable would be to provide music glasses in which an MP3 player on an IPod or the like is incorporated in the eyewear, either in a wired or wireless environment. Through the use of this type of system, a plurality of users could be networked via an MP3 player type environment within a hotspot, or the like, which would allow one to have downloads of whatever music is required through the eyeglasses. The system could allow for downloadable music which could be selected via scrolling and the like through voice recognition systems.

By connecting to a client-server network or Bluetooth wifi installation, for example, the eyeglasses could link to a multimedia network, authorize downloading and billing for selected music. By this means, access to a plurality of libraries for music selections could be provided.

It would also be possible to provide access to streaming audio media. Also, access can be provided to multimedia libraries, etc., via the client/server model.

Information could be received via a digital client/server model enabled to work with iPods or MP3 players. Similarly, bluetooth wireless technology could be utilized to provide access to music and live audio sources.

The eyewear could also be utilized in conjunction with wireless technology to allow a user or a plurality of users to participate simultaneously in single or group karaoke singing. The eyewear could be used specifically to display the lyrics of a song, melody, notes, name of the song or other associated references.

It would also be possible to receive and listen to AM or FM radio signals, via an AM/FM radio tuner connected to the eyewear hardware.

In this type of environment, the headphones can be either digital or analog. The user doesn't need to have 10,000 songs, for example. They can come enrolled in an in-song virtual network library upon entering a hotspot. Therefore, the local storage 306 could be limited. In addition, this would provide location identity information for one who is using the network. The songs can be streamed as well as downloaded. The songs could be purchase using the eyewear. The system could be scaleable; depending upon what kind of device was being used.

3. Telecommunications Environment

Figure 4:
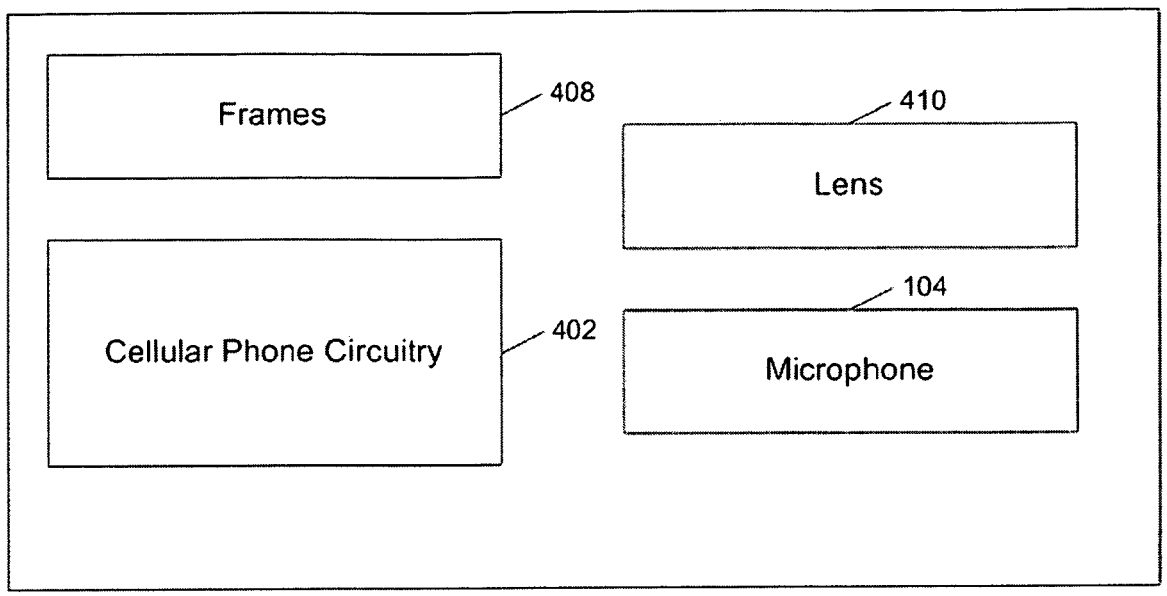
FIG. 4 is a block diagram that illustrates eyewear that is utilized as a cell phone.
Figure 5:
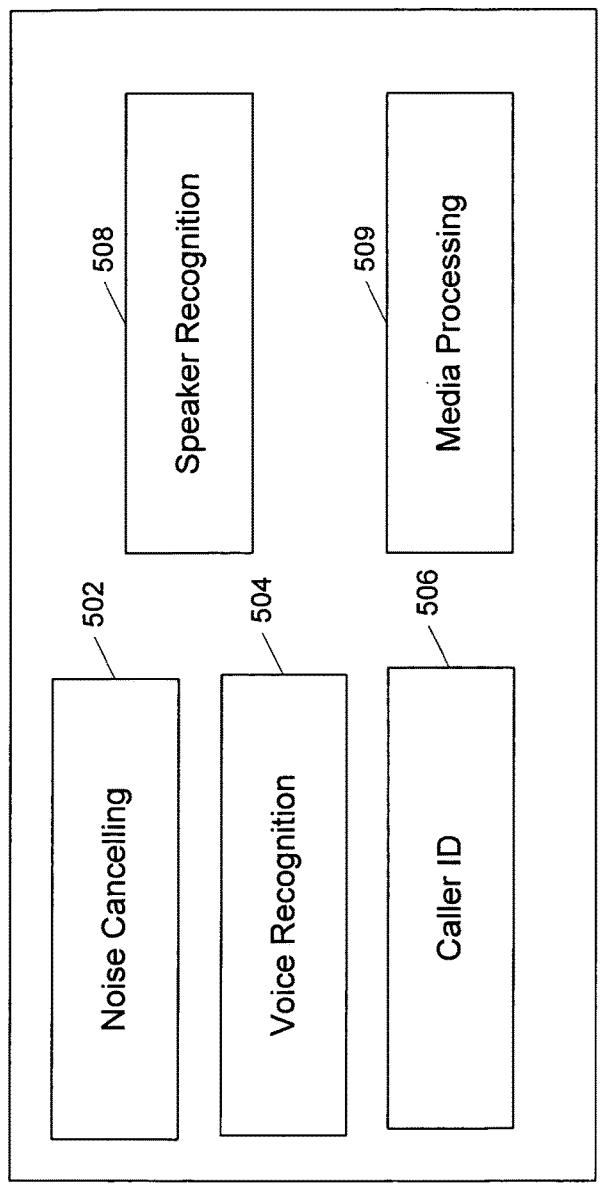
FIG. 5 is a block diagram that illustrates the cellular phone circuitry of FIG. 4.

FIG. 4 is a block diagram that illustrates eyewear that is utilized as a cell phone 400. FIG. 4 comprises cellular phone circuitry 402, a microphone 104, frames 408 and one or a plurality of lenses 410. The cell phone eyewear 400 could be implemented utilizing digital telephone technology. Circuitry 402 within the eyewear could be utilized to allow a telephone number or other visual information such as that provided by multimedia messaging services to be displayed on the lens 410 of the eyewear as shown in FIG. 3. FIG. 5 is a block diagram that illustrates the cellular phone circuitry of FIG. 4. FIG. 5 comprises noise cancelling circuitry 502, voice recognition circuitry 504, caller ID circuitry 506 and speaker recognition circuitry 508 and media processing circuits 509. The telephone number could be activated via the digital circuitry 402 as part of the media focals 100. In addition, the circuitry could be made truly digital via a digital signal processor which is coupled to a camera otherwise in the environment. The above system would allow for voice recording through use of a microphone 104 and would allow for voice recognition through use of the voice recognition circuitry 504, which would allow for signal conditioning on the cell phone in a variety of ways.

The cell phone environment 402 provides a plurality of areas for improvement utilizing existing technologies. Firstly, one of the major annoyances in cell phone use is that the users have to speak in a loud manner because of background noise and the like. There are a variety of reasons for this problem including the placement of the microphone of the cell phone relative to the speaker's mouth, due to the aforementioned background noise, and other issues. By placing the microphone 104 strategically on the eyewear such as near the noise or mouth the user will not have to speak as loudly. The microphone could also be located in flip down microphones. In addition noise canceling circuitry 502 could be utilized to remove the background noise. The microphone capability would include the advantage of utilizing noise rejection techniques. Buttons located on the eyewear can be utilized to control features thereon. Finally, the microphone 104 could utilize whisper technology such that the speaker will not have to speak as loudly.

The eyewear would in a preferred embodiment include voice recognition circuitry 504 and caller ID circuitry 506. The conventionality for hearing and talking in a preferred embodiment would be located in ear and nose pad portions of glasses. Referring back to FIG. 3, the electronics for the cell phone in a preferred embodiment would be within the frame 308 of the eyewear. In addition the eyewear would include a fully integrated information bar 302. Finally, a speaker recognition algorithm 508 as shown in FIG. 5 would allow only the voice of the user to be recognized and the background noise would be cancelled. Accordingly, the unique characteristics of the speaker are provided via an audible model.

This can performed utilizing a variety of methods. For example analyzing the voice of the user and combining the analysis with noise cancellation. In another example the user can talk softly and cancel noise and a directional microphone is used which takes advantage of device location.

Similar to the media focal and MP3 player environments, a digital client/server or Bluetooth/wifi model could be adapted to link the eyewear to external communication equipment. Such equipment could include digital cell phones, PDAs or wifi enabled PCs or other devices. Such an embodiment could enable review of voicemail, screen viewed emails, text to speech audio email conversions, multimedia messaging services, and other data sources.

Wireless or Bluetooth interconnection could also make possible VOIP glasses to be utilized instead of a cell phone. Other features enabled by a wireless link could link the eyeware to MP3 devices, an iPod, a printer, wireless/wired TV, coupons, and the like. Also "FDA glasses" could provide built in a time display, alarm calendar, interfacing with PCs or network sources, a speaker and the like.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. Eyewear including
   a frame member;
   circuitry coupled to the frame member, disposed to enhance use of the eyewear;
   an eye sensor coupled to the frame member, the eye sensor disposed to activate the circuitry in response to a sequence of two or more eye voluntary eye gestures by a user, using activity of the eye itself of a user;
   wherein the eye sensor is responsive to voluntary eye gestures by the user without presentation of an image for the user to review;
   wherein each voluntary eye gesture includes one or more of: intentional blinking more than once in succession, facial and eye movements, squinting, or combinations of intentional blinking and facial or eye movements;
   wherein the circuitry provides one or more functions of: receiving, recording, playing, or presenting, audio information.

2. Eyewear as in claim 1, wherein
   downloading and billing for selected music or audio is authorized;
   simultaneous access to a plurality of libraries for music or audio selections is provided,
   wherein the access can be free of charge, or in response to a payment.

3. Eyewear as in claim 1, wherein
   the circuitry is disposed to access audio media using one or more of:
   computer networks, external audio players, external devices, or wireless technology.

4. Eyewear as in claim 1, wherein
   the circuitry is disposed to access one or more of:
   computer networks, streaming audio media, music or audio selection libraries, or multimedia libraries.

5. Eyewear as in claim 1, wherein
   the circuitry is disposed to provide access in response to a payment, to one or more of:
   streaming audio media, music or audio selection libraries, or multimedia libraries.

6. Eyewear as in claim 1, wherein
   the circuitry is disposed to download or select audio or music input in response to one or more of:
   scrolling, or voice recognition.

7. Eyewear as in claim 1, wherein
the circuitry is disposed to network a plurality of users in an audio or music player environment.
8. Eyewear as in claim 1, wherein
the circuitry is disposed to provide audio information in one or more of:
a wired environment, or a wireless environment.
9. Eyewear as in claim 1, wherein
the circuitry is disposed to provide a plurality of user with free, purchased, or billed, access to one or more of:
song lyrics, song melodies, song notes, song names, or information with respect to a song.
10. Eyewear as in claim 1, wherein
the circuitry is disposed to provide access to a virtual network library.
11. Eyewear as in claim 10, wherein
the virtual network library includes one or more of:
association with a hotspot, association with a wi-fi hotspot, providing enrollment of users upon entering a hotspot, providing location information for users using the hotspot, providing streaming audio associated with a hotspot, providing downloading audio associated with a hotspot, or providing purchasing audio using the eyewear.
12. Eyewear as in claim 1, wherein
the circuitry is disposed to provide information from one or more of:
a radio station, or a music or audio player.
13. Eyewear as in claim 1, wherein
the circuitry is disposed to provide selection of the information from one or more of:
audio libraries, or multimedia libraries.
14. Eyewear including
a wearable element;
circuitry coupled to the wearable element, disposed to enhance use of the eyewear;
a wearable sensor coupled to the wearable element, the wearable sensor disposed to activate the circuitry in response to a sequence of two or more voluntary eye gestures by a user, using activity of the eye, face, or head, of a user;
wherein the eye sensor is responsive to voluntary eye gestures by the user without presentation of an image for the user to review;
wherein each voluntary eye gesture includes one or more of: intentional blinking more than once in succession, facial and eye movements, squinting, or combinations of intentional blinking and facial or eye movements;
wherein the circuitry is disposed to provide one or more functions of: receiving, recording, playing, or presenting, one or more of: audio, visual, or digital, information.
15. Eyewear as in claim 14, wherein
the circuitry is disposed to access audio media using one or more of:
simultaneous access to a computer network, an external audio player, an external device, or wireless technology.
16. Eyewear as in claim 14, wherein
the circuitry is disposed to access one or more of:
computer networks, streaming audio media, one or more music or audio selection libraries, or one or more multimedia libraries,
wherein the access can be free of charge, or in response to a payment.
17. Eyewear as in claim 14, wherein
the circuitry is disposed to authorize one or more of: downloading selected music or audio, billing for selected music or audio, or free or billed access to one or more libraries from which music or audio is selectable.
18. Eyewear as in claim 14, wherein
the circuitry is disposed to control or to provide audio information in one or more of:
a wired environment, or a wireless environment.
19. Eyewear as in claim 14, wherein
the circuitry is disposed to download or select audio or music input in response to one or more of:
scrolling, or voice recognition.
20. Eyewear as in claim 14, wherein
the circuitry is disposed to network a plurality of users in an audio or music player environment.
21. Eyewear as in claim 14, wherein
the circuitry is disposed to provide a plurality of user with simultaneous participation in one or more of:
joint singing, or karaoke singing.
22. Eyewear as in claim 14, wherein
the circuitry is disposed to provide a plurality of users with free or billed access to one or more of:
song lyrics, song melodies, song notes, song names, or information with respect to a song.
23. Eyewear as in claim 14, wherein
the circuitry is disposed to provide access to a virtual network library,
free of charge or in response to a payment.
24. Eyewear as in claim 23, wherein
the virtual network library includes one or more of:
association with a hotspot, association with a wi-fi hotspot, providing enrollment of users upon entering a hotspot, providing location information for users using the hotspot, providing streaming audio associated with a hotspot, providing downloading audio associated with a hotspot, or providing purchasing audio using the eyewear.
25. Eyewear as in claim 14, wherein
the circuitry is disposed to provide information from an external device.
26. Eyewear as in claim 25, wherein
the external device includes one or more of:
a computer network, a music or audio player, a radio station, or a server.
27. Eyewear as in claim 14, wherein
the circuitry is disposed to provide one or more of:
linking to a multimedia network, or receiving information to one or more libraries of selections therefrom,
for selected music or audio information.
28. Eyewear as in claim 14, wherein
the circuitry is disposed to provide selection of the information from one or more of:
music or audio libraries, or multimedia libraries.
29. Eyewear as in claim 14, wherein
the circuitry is disposed to select among the
one or more music or audio selection libraries, or one or more multimedia libraries.
30. Eyewear as in claim 14, wherein
the circuitry is disposed to use wireless technology to access one or more of:
music, audio, or live audio sources.

* * * * *